(12) United States Patent
Agnew, V et al.

(10) Patent No.: US 12,396,657 B2
(45) Date of Patent: Aug. 26, 2025

(54) NON-LINEAR SINGLE AXIS NAVIGATION SENSOR WITH STRAIN RELIEF

(71) Applicant: Biosense Webster (Israel) Ltd., Yokneam (IL)

(72) Inventors: William James Agnew, V, Irvine, CA (US); Hamid Massoud, Irvine, CA (US); Corey M. Rousu, Huntington Beach, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 366 days.

(21) Appl. No.: 17/376,251

(22) Filed: Jul. 15, 2021

(65) Prior Publication Data

US 2022/0346663 A1    Nov. 3, 2022

Related U.S. Application Data

(60) Provisional application No. 63/181,641, filed on Apr. 29, 2021.

(51) Int. Cl.
*A61B 5/06* (2006.01)
*A61B 5/00* (2006.01)
*A61B 34/20* (2016.01)

(52) U.S. Cl.
CPC ............ *A61B 5/062* (2013.01); *A61B 5/6852* (2013.01); *A61B 2034/2046* (2016.02); *A61B 2562/187* (2013.01); *A61B 2562/22* (2013.01)

(58) Field of Classification Search
None
See application file for complete search history.

(56) References Cited

U.S. PATENT DOCUMENTS

| | | |
|---|---|---|
| 4,815,478 A | 3/1989 | Buchbinder et al. |
| RE34,502 E | 1/1994 | Webster, Jr. |
| 5,275,151 A | 1/1994 | Shockey et al. |
| 5,391,199 A | 2/1995 | Ben-Haim |
| 5,395,329 A | 3/1995 | Fleischhackor et al. |
| 5,443,489 A | 8/1995 | Ben-Haim |

(Continued)

FOREIGN PATENT DOCUMENTS

| | | |
|---|---|---|
| EP | 1 457 226 A2 | 3/2004 |
| EP | 1 562 665 | 6/2004 |

(Continued)

OTHER PUBLICATIONS

Extended European Search Report dated Sep. 28, 2022, from corresponding European Application No. 22170560.1.

*Primary Examiner* — Pascal M Bui Pho
*Assistant Examiner* — Michael S Kellogg

(57) ABSTRACT

The distal end of the catheter can be constructed to include one or more features to provide strain relief to wiring of multiple single axis sensors. In some examples, the multiple single axis sensors and associated wiring can be manufactured over a flexible tube that can be placed over a movable support member. In some examples, wiring can be wound an increased number of consecutive traverse turns on a distal and/or proximal side of a single axis sensor, and a shrink sleeve may be positioned over the traverse turns. In some examples a wire shield transition point can be positioned on a straight portion in a proximal direction to the distal portion of the catheter.

18 Claims, 16 Drawing Sheets

(56) References Cited

U.S. PATENT DOCUMENTS

| | | | |
|---|---|---|---|
| 5,645,065 A | 7/1997 | Shapiro et al. |
| 5,656,029 A | 8/1997 | Imran et al. |
| 5,891,088 A | 4/1999 | Thompson et al. |
| 5,997,473 A | 12/1999 | Taniguchi et al. |
| 6,123,699 A | 9/2000 | Webster, Jr. |
| 6,171,277 B1 | 1/2001 | Ponzi |
| 6,183,463 B1 | 2/2001 | Webster, Jr. |
| 6,484,118 B1 | 11/2002 | Govari |
| 6,491,681 B1 | 12/2002 | Kunis et al. |
| 6,500,129 B1 | 12/2002 | Mahurkar |
| 6,554,794 B1 | 4/2003 | Mueller et al. |
| 6,574,492 B1 | 6/2003 | Ben-Haim et al. |
| 6,690,963 B2 | 2/2004 | Ben-Haim et al. |
| 6,788,967 B2 | 9/2004 | Ben-Haim et al. |
| 6,892,090 B2 | 5/2005 | Verard et al. |
| 6,961,602 B2 | 11/2005 | Fuimaono et al. |
| 7,174,202 B2 | 2/2007 | Bladen et al. |
| 7,274,957 B2 | 9/2007 | Drysen |
| 7,615,044 B2 | 11/2009 | Scheibe et al. |
| 7,931,616 B2 | 4/2011 | Selkee |
| 8,118,775 B2 | 2/2012 | Grunewald et al. |
| 8,259,505 B2 | 9/2012 | Oyama |
| 8,382,662 B2 | 2/2013 | Soper et al. |
| 8,529,505 B2 | 9/2013 | Grunewald et al. |
| 8,700,133 B2 | 4/2014 | Hann |
| 8,792,962 B2 | 7/2014 | Esguerra et al. |
| 8,805,472 B2 | 8/2014 | Iglesias |
| 8,880,147 B2 | 11/2014 | Tegg et al. |
| 8,926,528 B2 | 1/2015 | Govari et al. |
| 8,936,583 B2 | 1/2015 | Holzbauer et al. |
| 10,405,774 B2 | 9/2019 | Esguerra Wilczynski et al. |
| 2003/0028096 A1 | 2/2003 | Niwa et al. |
| 2003/0160721 A1 | 8/2003 | Gilboa et al. |
| 2005/0274425 A1 | 12/2005 | Ostrander et al. |
| 2007/0164900 A1 | 7/2007 | Schneider et al. |
| 2008/0255540 A1 | 10/2008 | Selkee |
| 2009/0005754 A1 | 1/2009 | Soetermans |
| 2009/0192412 A1 | 7/2009 | Sela et al. |
| 2010/0036285 A1* | 2/2010 | Govari ............ A61B 5/062 600/377 |
| 2010/0069834 A1 | 3/2010 | Schultz |
| 2010/0168827 A1 | 7/2010 | Schultz |
| 2010/0222664 A1 | 9/2010 | Lemon et al. |
| 2011/0054287 A1 | 3/2011 | Schultz |
| 2012/0143088 A1 | 6/2012 | Schultz |
| 2012/0172842 A1 | 7/2012 | Sela et al. |
| 2014/0228838 A1 | 8/2014 | Kirschenman |
| 2014/0275957 A1 | 9/2014 | Lupotti |
| 2020/0015703 A1* | 1/2020 | Esguerra Wilczynski ............ A61B 5/341 |
| 2021/0001084 A1 | 1/2021 | Highsmith et al. |

FOREIGN PATENT DOCUMENTS

| | | |
|---|---|---|
| EP | 2 151 209 A2 | 8/2009 |
| EP | 2 165 730 A1 | 9/2009 |
| EP | 2 301 617 A1 | 9/2010 |
| EP | 2 460 558 A1 | 12/2011 |
| EP | 2 897 524 | 7/2014 |
| JP | 2010-36040 A | 2/2010 |
| WO | WO 96/34652 A1 | 11/1996 |
| WO | WO 2007/130720 A1 | 11/2007 |

* cited by examiner

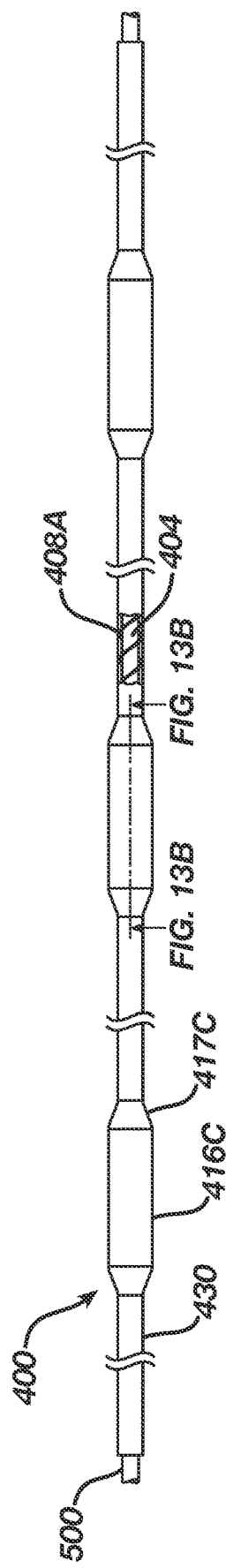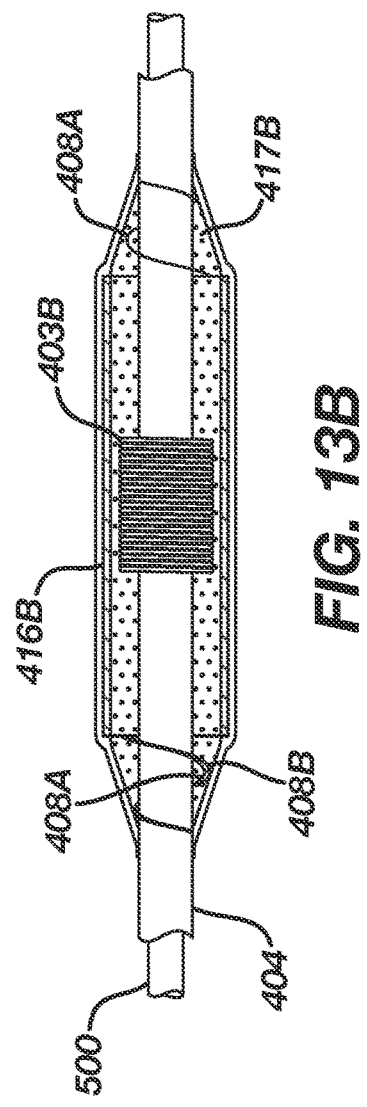
FIG. 13A
FIG. 13B

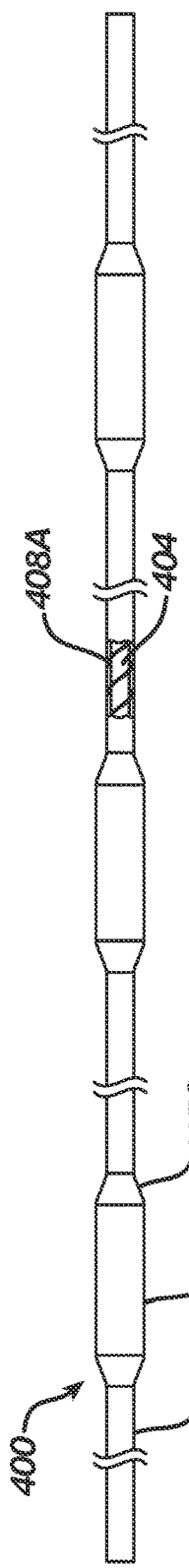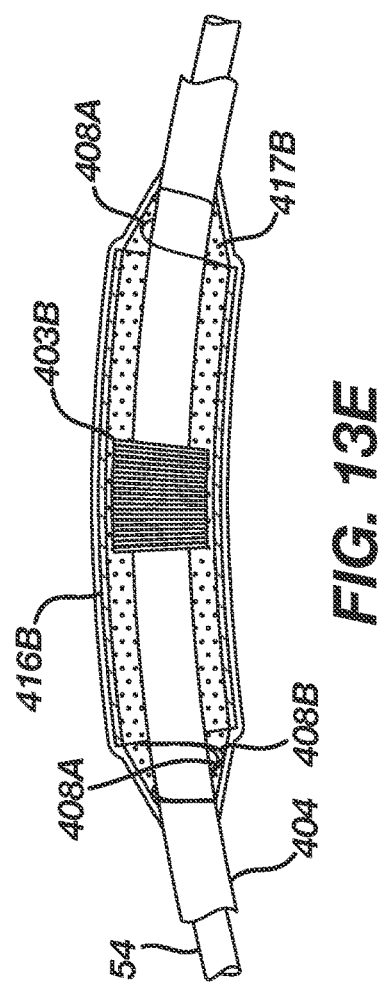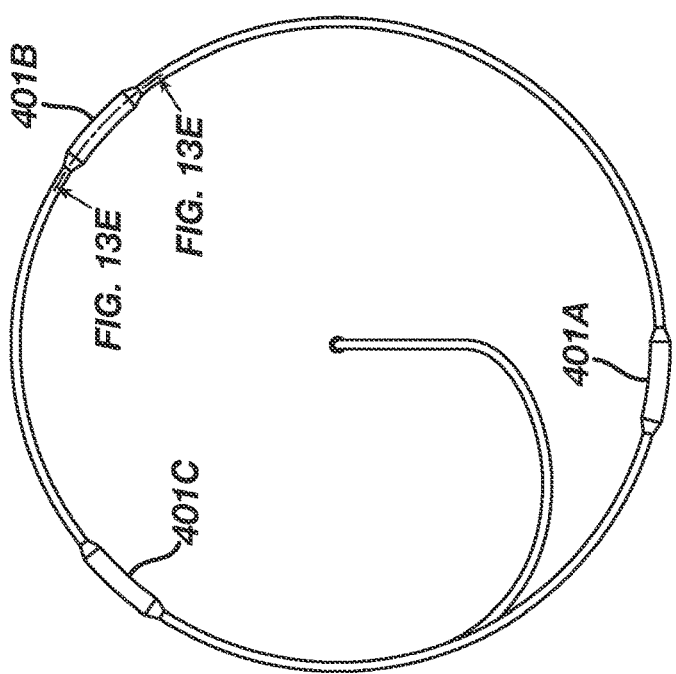
FIG. 13C
FIG. 13E
FIG. 13D

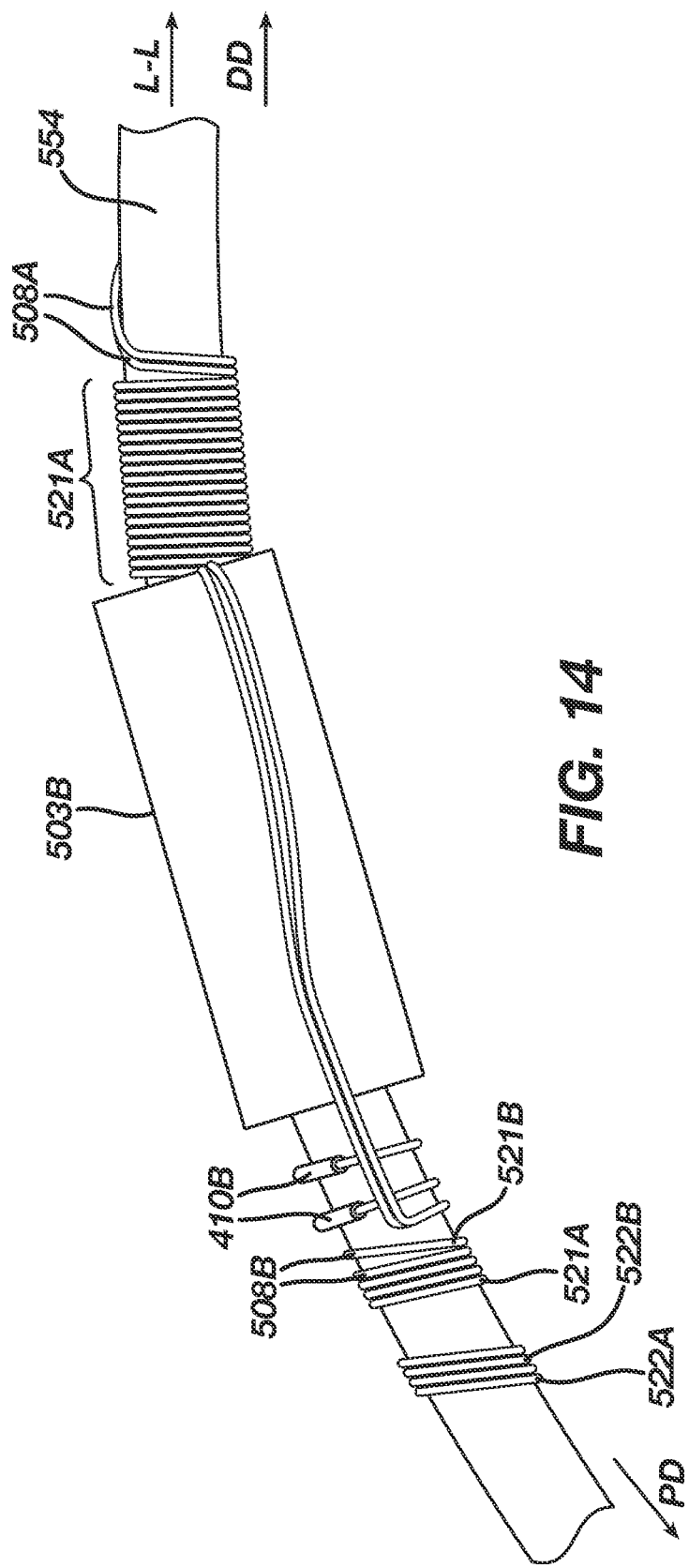

NON-LINEAR SINGLE AXIS NAVIGATION SENSOR WITH STRAIN RELIEF

CROSS REFERENCE TO RELATED APPLICATIONS

This application claims the benefit of priority under the Paris Convention as well as 35 U.S.C. §§ 119 and 120 to prior filed U.S. Provisional Patent Application No. 63/181,641 filed on Apr. 29, 2021 which is hereby incorporated by reference as set forth in full herein.

FIELD

This invention relates to a catheter, in particular, a catheter having location sensors mounted on a flexible, non-linear distal end portion for improved position sensing of the distal end portion.

BACKGROUND

A magnetic field can be sensed by positioning a conductive coil in the magnetic field and observing electrical current and/or voltage induced in the coil by a change in the magnetic field that is aligned with an axis of the conductive coil. Because electrical current is induced in the conductive coil, such a coil is also referred to as an inductive coil. Relative position of a sensor including one or more inductive coils can be determined in relation to a known magnetic field source by monitoring the induced electric current and/or voltage of the inductive coil(s).

An inductive coil wrapped around a flexible catheter structure can deflect causing strain on coil wiring. In such cases, kinking or breakage of wiring can occur.

SUMMARY

Examples presented herein generally include a sensor assembly having inductive coils wound about a tubular member that can be positioned over a support member at a distal portion of a catheter. The sensor assembly can be part of a navigation system which uses electrical currents induced in the inductive coils in the sensor assembly to determine a position of the distal portion of the catheter when the distal portion is positioned within a known magnetic field. The tubular member can be configured to relieve strain on the inductive coils and/or wiring of the sensor assembly as the support member flexes to reshape the distal portion of the catheter. Each of the inductive coils can be co-axial to the tubular member, such that each inductive coil functions respectively as a single axis sensor (SAS).

An example SAS assembly can include a tubular member, a distal inductive coil, a first dual cable, and a proximal inductive coil. The tubular member can have a lumen therethrough sized to receive an elongated support member suitable for shaping a distal section of a mapping catheter. The lumen can have a diameter measuring from approximately 0.1 mm to about 0.25 mm. The distal inductive coil can be affixed to the tubular member and coaxial to the tubular member. The distal inductive coil can include leads. The first dual cable can be electrically joined to the leads of the distal inductive coil and wound over the tubular member. The proximal inductive coil can be affixed to the tubular member across (over and/or under) the first dual cable. The proximal inductive coil can be coaxial to the tubular member. The proximal inductive coil can be separated from the distal inductive coil such that the distal inductive coil moves in relation to the proximal inductive coil when the tubular member is moved from a linear configuration to a nonlinear configuration. The nonlinear configuration can be approximately circular with a circumference measuring from approximately 30 millimeters to approximately 80 millimeters.

The SAS assembly can further include an intermediate inductive coil affixed to the tubular member, coaxial to the tubular member, positioned between the distal inductive coil and the proximal inductive coil when the SAS assembly is in the linear configuration, and positioned such that the proximal inductive coil, intermediate inductive coil, and distal inductive coil collectively function as a three-axis sensor when the SAS assembly is in the nonlinear configuration.

The SAS assembly can further include a second dual cable electrically joined to leads of the intermediate inductive coil and wound over the tubular member to cross (over and/or under) the proximal inductive coil.

The nonlinear configuration can be approximately circular. The proximal inductive coil, intermediate inductive coil, and distal inductive coil can be positioned approximately equidistant around a circumference of the nonlinear configuration.

An example mapping catheter and can include an elongated support member extending through a distal section of the mapping catheter and a SAS assembly. The SAS assembly of the example catheter can be configured similarly to the above example SAS assembly. The SAS assembly can be manufactured separately from the elongated support member, and the elongated support member can be inserted into the SAS assembly.

The SAS assembly can include a tubular member surrounding the elongated support member, a distal inductive coil affixed to the tubular member, and a proximal inductive coil affixed to the tubular member. The elongated support member can have a nonlinear predetermined configuration to which the elongated support member moves when the distal section is disposed within a patient. The distal inductive coil and the proximal inductive coil can each be coaxial to the tubular member. The proximal inductive coil and the distal inductive coil can be separated from each other such that the distal inductive coil moves in relation to the proximal inductive coil when the elongated support member moves to the nonlinear predetermined configuration. The elongated support member can include a memory shape material heat set to the nonlinear predetermined configuration. The SAS sensor assembly can further include a first dual cable electrically joined to leads of the distal inductive coil and wound over the tubular member to cross (over and/or under) the proximal inductive coil.

The SAS sensor assembly can further include intermediate inductive coil affixed to the tubular member, coaxial to the tubular member, and positioned between the distal inductive coil and the proximal inductive coil when the elongated support member is linearly elongated. The proximal inductive coil, intermediate inductive coil, and distal inductive coil can collectively function as a three-axis sensor when the elongated support member moves to the nonlinear predetermined configuration.

The nonlinear predetermined configuration can be approximately circular. The proximal inductive coil, intermediate inductive coil, and distal inductive coil can be positioned approximately equidistant around a circumference of the nonlinear predetermined configuration. The nonlinear predetermined configuration can have a circumference measuring from approximately 10 millimeters to approximately 50 millimeters.

The SAS sensor assembly can further include a second dual cable electrically joined to leads of the intermediate inductive coil and wound over the tubular member to cross the proximal inductive coil.

Another example mapping catheter can include an elongated body, a distal section distal to the elongated body, an elongated support member extending through the distal section, a tubular member surrounding the elongated support member, a distal inductive coil affixed to the tubular member, and a proximal inductive coil affixed to the tubular member. The distal section can be movable from a linear delivery configuration to a nonlinear deployed configuration. The elongated support member can be shaped to move the distal section into the nonlinear deployed configuration. The elongated support member can include a memory shape material heat set to a nonlinear predetermined configuration that approximates the nonlinear deployed configuration of the distal section. The distal inductive coil and proximal inductive coil can respectively be coaxial to the tubular member. The proximal inductive coil can be separated from the distal inductive coil such that the distal inductive coil moves in relation to the proximal inductive coil when the distal section moves from the linear delivery configuration to the nonlinear deployed configuration. The mapping catheter can further include a first dual cable electrically joined to leads of the distal inductive coil and wound over the tubular member to cross (over and/or under) the proximal inductive coil.

The mapping catheter can further include an intermediate inductive coil affixed to the tubular member, coaxial to the tubular member, and positioned between the distal inductive coil and the proximal inductive coil when the distal section is in the linear delivery configuration. The proximal inductive coil, intermediate inductive coil, and distal inductive coil can collectively function as a three-axis sensor when the distal section is in the nonlinear deployed configuration.

The nonlinear deployed configuration can be approximately circular. The proximal inductive coil, intermediate inductive coil, and distal inductive coil can be positioned approximately equidistant around a circumference of the distal section in the nonlinear deployed configuration. The nonlinear deployed configuration can have a circumference measuring from approximately 10 millimeters to approximately 50 millimeters.

The mapping catheter can further include a second dual cable electrically joined to leads of the intermediate inductive coil and wound over the tubular member to cross the proximal inductive coil.

The mapping catheter can further include a control handle proximal of the elongated body, a contraction wire, and/or ring electrodes circumscribing the distal section. The contraction wire can extend through the elongated body and distal section. The contraction wire can be manipulated to shape the nonlinear deployed configuration. The ring electrodes can be configured to receive electrical signals from tissue during a patient treatment.

An example method can include some or all of the following steps that can be executed in various orders, and the method can include additional steps not listed. A first inductive coil can be wound around a tubular member positioned over a mandrel. A first dual cable electrically joined to leads of the first inductive coil can be wound around the tubular member. A second inductive coil can be wound around the tubular member such that the first dual cable crosses (over and/or under) the second inductive coil and the second inductive coil is separated from the first inductive coil such that when the tubular member is flexed into a nonlinear configuration the first inductive coil moves in relation to the second inductive coil.

The method can further include flexing the tubular member, with the first inductive coil, first dual cable, and second inductive coil thereon into an approximately circular shape with a circumference measuring from approximately 30 millimeters to approximately 80 millimeters.

The method can further include extending an elongated support member having a predetermined shape through a lumen of the tubular member. The elongated support member can be extended through the lumen of the tubular member after winding the first inductive coil around the tubular member, after winding the first dual cable around the tubular member, and after winding the second inductive coil around the tubular member. The method can further include moving the elongated support member into the predetermined shape thereby forcing the tubular member into the nonlinear configuration.

The method can further include winding an intermediate inductive coil around the tubular member at a position between the first inductive coil and the second inductive coil when the tubular member is linear, such that the first inductive coil, intermediate inductive coil, and second inductive coil collectively function as a three-axis sensor when the tubular member is in the nonlinear configuration, and such that the first dual cable crosses (over and/or under) the intermediate inductive coil.

The method can further include winding a second dual cable electrically joined to leads of the intermediate inductive coil around the tubular member to cross the second inductive coil.

The method can further include positioning the first inductive coil, intermediate inductive coil, and second inductive coil such that when the tubular member is in a circular shape, the first inductive coil, intermediate inductive coil, and second inductive coil are approximately equidistant from each other around the circular shape.

Another example mapping catheter can include coils of single axis sensors, dual cables electrically connected to a respective coil of a respective single axis sensor, and a shrink sleeve. Each dual cable can be respectively wound for about 5 to about 7 consecutive traverse turns of approximately 720° around a tubular member or directly around a support member on a distal and/or proximal side of the respective coil. The shrink sleeve can be positioned to completely cover the traverse turns. The example mapping catheter can further include a shield wire transition point positioned on a straight region of a distal end section of the mapping catheter.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIGS. 13A through 13E is a flow diagram illustrating steps of constructing a distal end of an example catheter in accordance with the present invention.

FIG. 14 is a side view illustration of an intermediate sensor of a variation of the example catheter in accordance with the present invention.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

As used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

Figure 1:
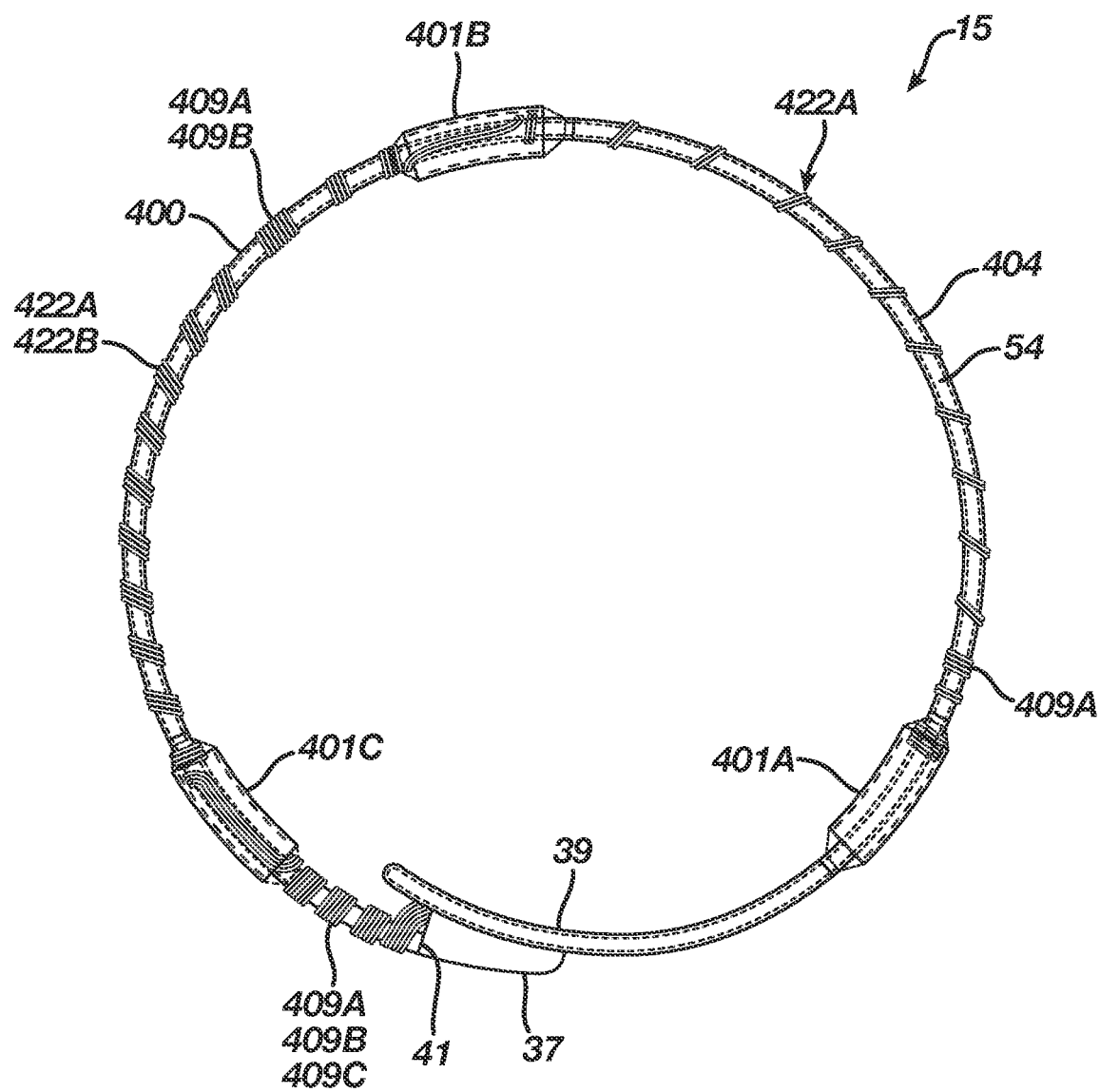
FIG. 1 is a top plan view illustration of an example nonlinear single axis sensor assembly in accordance with the present invention.
Figure 6:
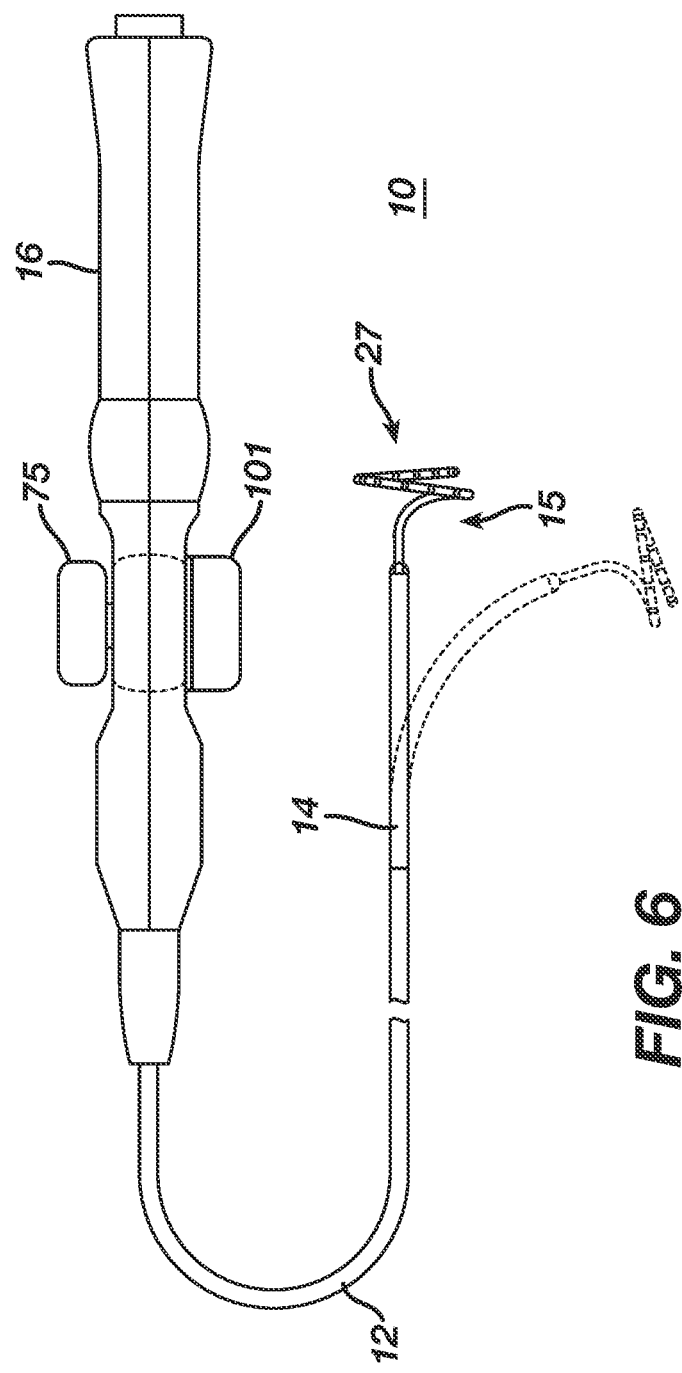
FIG. 6 is a top plan view illustration an example catheter in accordance with the present invention.

FIG. 1 illustrates a top plan view of a partially assembled circular region 39 of a distal end section 15 of a catheter (see example catheter 10 illustrated in FIG. 6). The circular region 39 is illustrated as including a nonlinear single axis sensor (SAS) assembly 400 including three sensors 401A, 401B, 401C configured to sense location and/or position of the circular region 39, cables 409A, 409B, 409C configured to carry electrical signals to and/or from each of the inductive sensors 401A, 401B, 401C respectively, and a tubular member 404 upon which the sensors 401A, 401B, 401C and the cables 409A, 409B, 409C are mounted. A support member 54 can extend through the tubular member 404 providing structure and shape to the distal end section 15. In some examples, the sensors 401A, 401B, 401C and cables 409A, 409B, 409C can be manufactured onto the tubular member 404 such the SAS assembly 400 is a component separate from the support member 54. The SAS assembly 400 can then slide onto the support member 54. The tubular member 404 can provide strain relief to the sensors 401A, 401B, 401C and/or cables 409A, 409B, 409C when the distal end section 15 flexes.

Figure 3:
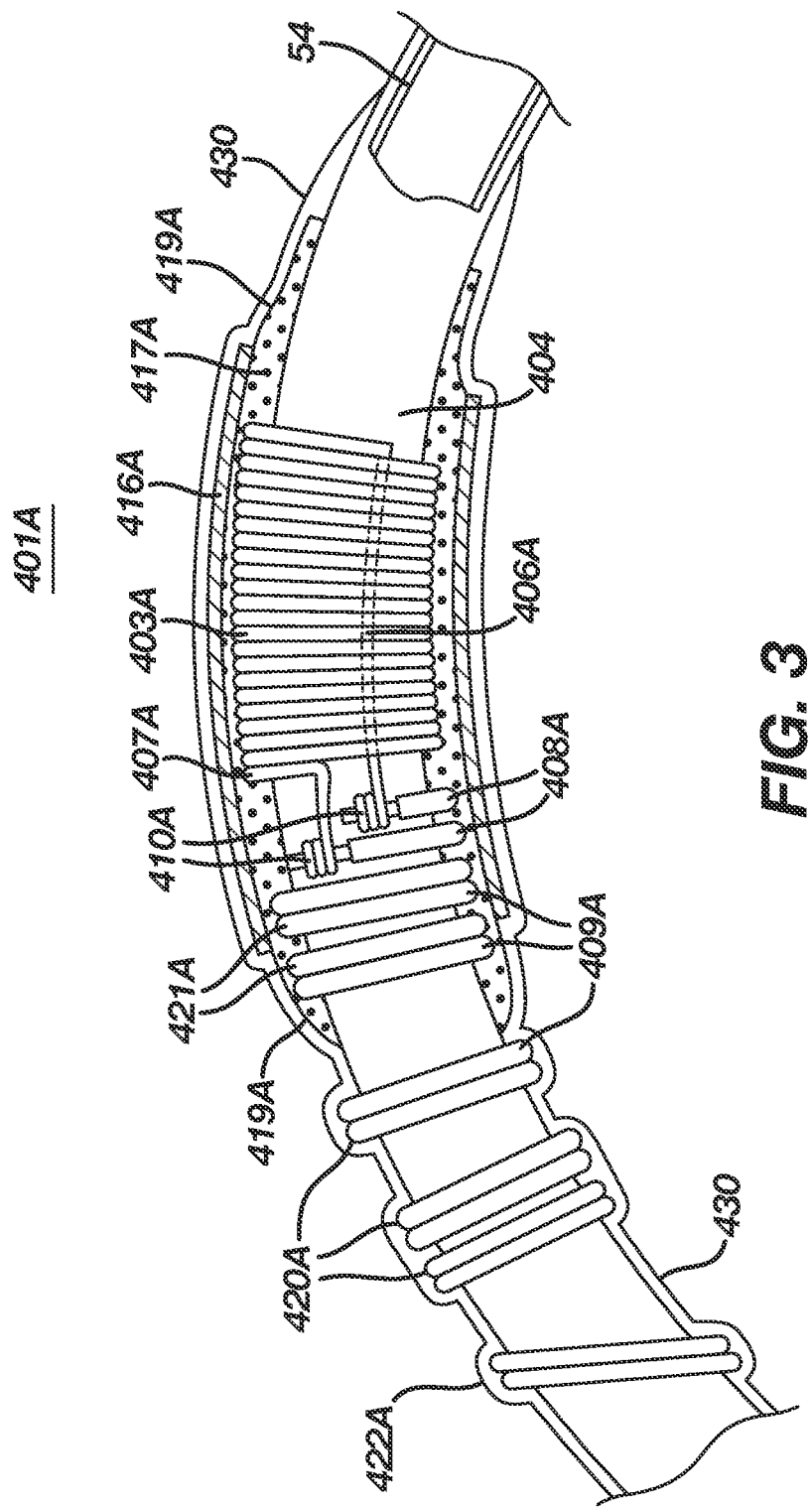
FIG. 3 is a side cut-away view illustration of an example distal sensor of the assembly in FIG. 1.
Figure 4:
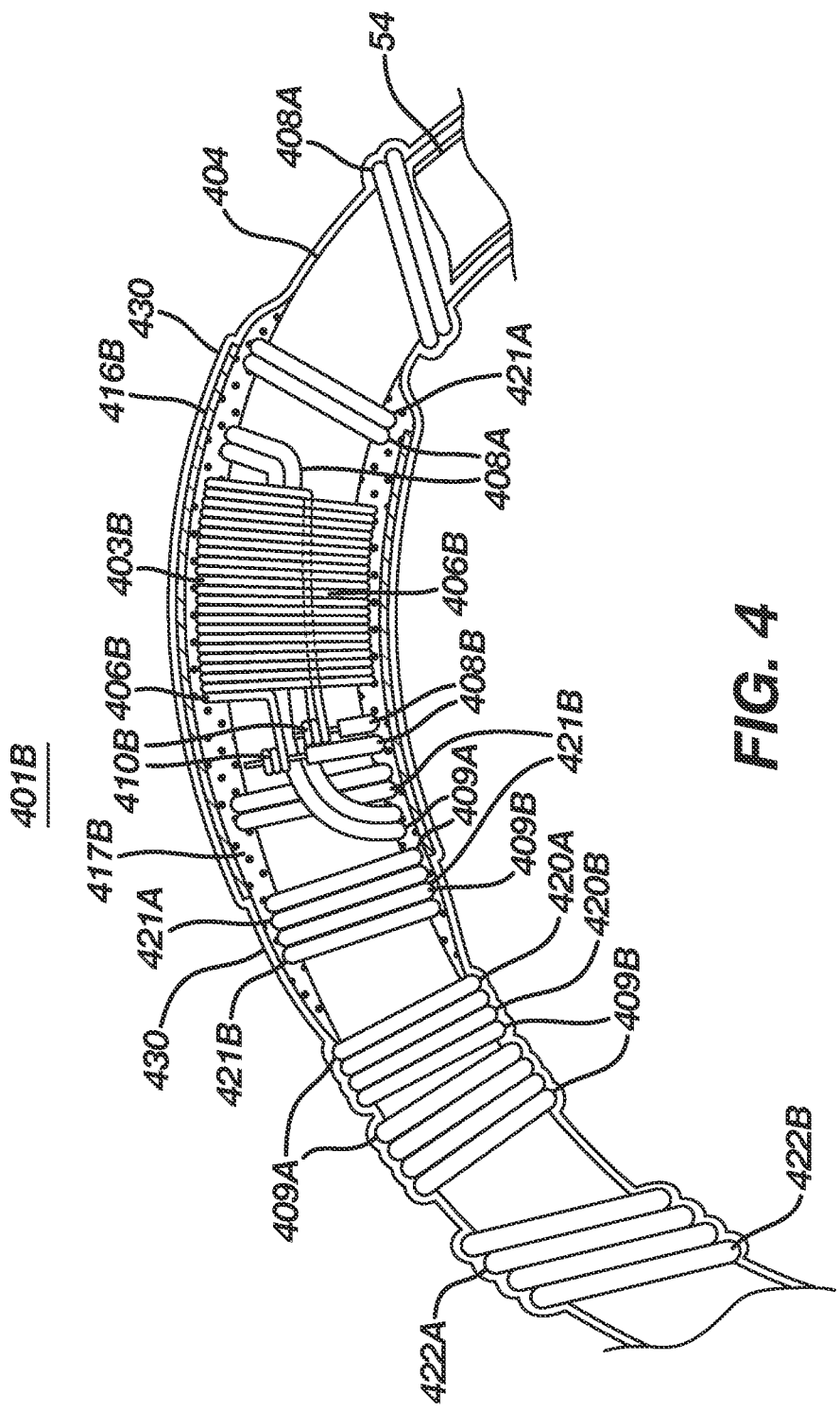
FIG. 4 is a side cut-away view illustration of an example of an intermediate sensor of the assembly in FIG. 1.
Figure 5:
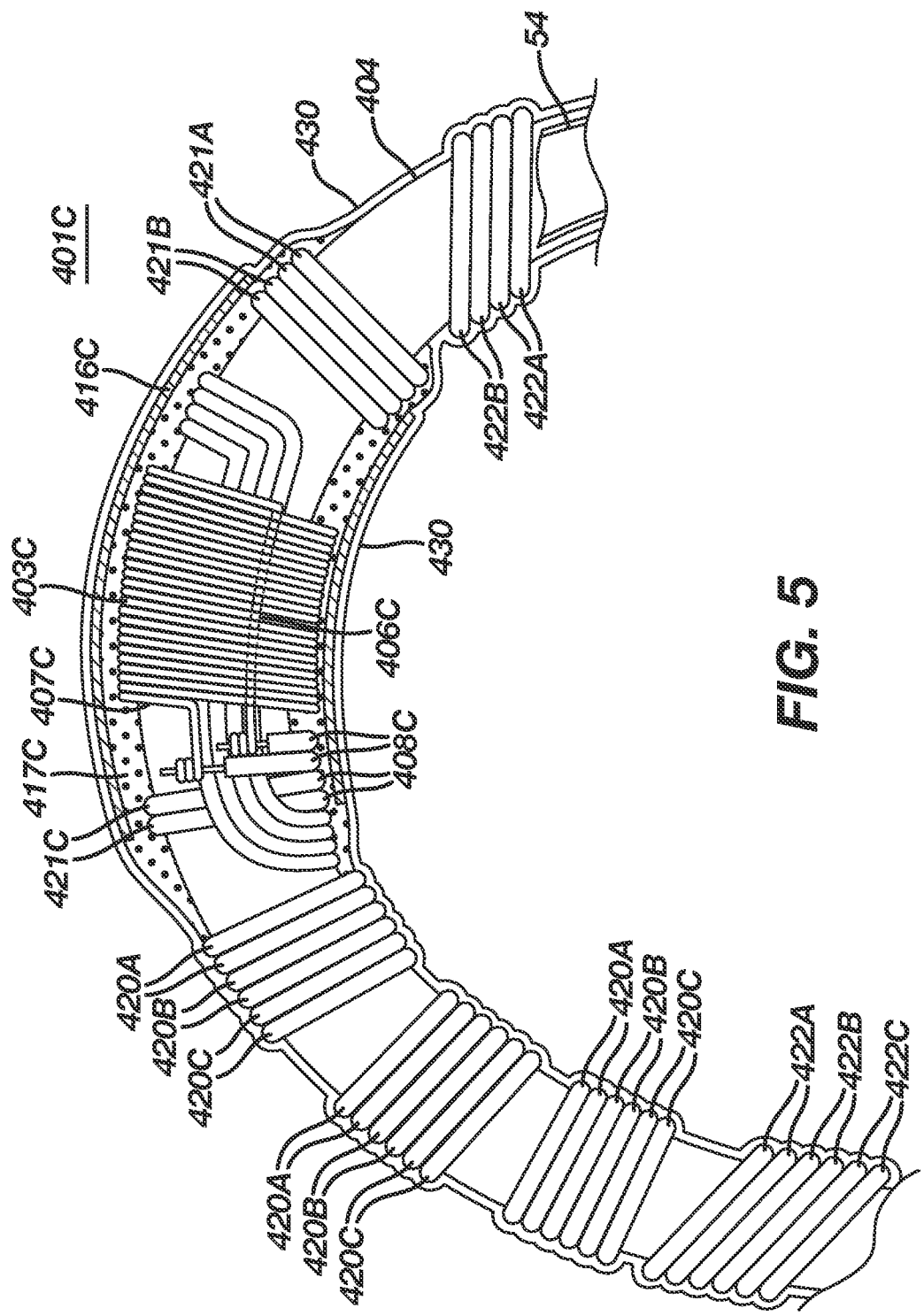
FIG. 5 is a side cut-away view illustration of an example proximal sensor of the assembly in FIG. 1.

Three single axis sensors 401A, 401B, 401C are illustrated positioned at equidistance from each other along the generally circular main region 39. A proximal sensor 401C is distal of an elbow 37 where the distal end section 15 bends to join a catheter shaft 14. An intermediate sensor 401B is about 120 degrees from the proximal sensor 401C. A distal sensor 401A is about 120 degrees from the intermediate sensor. Configured as such, the three sensors 401A, 401B, 401C can collectively function as a three-axis sensor. Details of each sensor 401A, 401B, 402C are illustrated in FIGS. 3 through 5 respectively.

Figure 2:
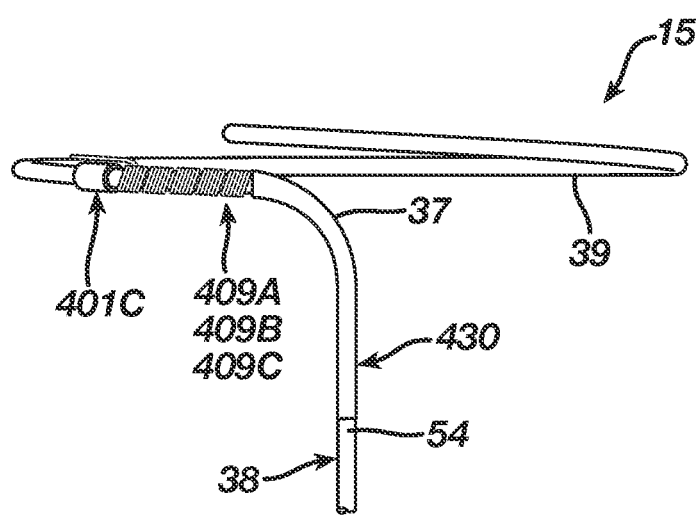
FIG. 2 is a side view illustration of the assembly in FIG. 1 with certain components removed for the sake of illustration.

FIG. 2 illustrates a side view of the distal end section 15 viewing the proximal sensor 401C and proximal portions of cables 409A, 409B, 409C with sensors and cable portions distal the proximal sensor 401C omitted for the sake of illustration. The sensors 401A, 401B, 401C enable the circular region 39 carrying the nonlinear SAS assembly 400 to be viewed under mapping systems such as those manufactured and sold by Biosense Webster, Inc., including the CARTO, CARTO XP, and NOGA mapping systems. Electrically, the sensors 401A, 401B, 401C can function similarly or identically to single axis sensors described in U.S. Pat. Nos. 8,792,962, 10,405,774, and U.S. Patent Publication No. 2020/0015703 each incorporated by reference herein; U.S. Pat. No. 8,792,962 is attached in the Appendix of U.S. Provisional Patent Application No. 63/181,641 to which the present application claims priority.

Referring collectively to FIGS. 1 and 2, the SAS assembly 400 can be configured to elongate to a substantially linear configuration when the distal end section 15 of the catheter is delivered through bodily lumens (e.g. blood vessels) and reshape to the circular shape illustrated or other nonlinear shape when deployed at a treatment site (e.g. heart chamber). The support member 54 can be made of a material having shape memory, i.e., that can be formed into a predetermined shape, straightened or bent out of its predetermined shape upon exertion of a force, and returned substantially to its predetermined shape upon removal of the force and/or application of heat. The movement and nonlinear shape of the SAS assembly 400 can be primarily determined by the properties of the support member 54. One suitable material for the support member 54 is a nickel/titanium alloy. Such alloys typically include about 55% nickel and 45% titanium but may include from about 54% to about 57% nickel with the balance being titanium. A suitable nickel/titanium alloy is Nitinol, which has excellent shape memory, together with ductility, strength, corrosion resistance, electrical resistivity, and temperature stability.

As the SAS assembly 400 moves between the linear delivery shape to the deployed nonlinear shape, the tubular member 404 can provide strain relief to the sensors 401A, 401B, 401C and/or cables 409A, 409B, 409C by providing an indirect coupling to the support member 54 as opposed to a more direct coupling such as adhesion (e.g. with epoxy) to the support member 54. The tubular member 404 can be configured to be able to slide against the support member 54 and/or skew or flex to a certain degree, essentially allowing the sensors and cables to ride as if "on rollers" over the support member 54. In a similar manner, the tubular member 404 can act as a strain relief between a support member and sensor assembly for numerous other support member shapes and sensor configurations as understood by a person skilled in the pertinent art according to the teachings herein.

Because the sensors 401A, 401B, 401C are not directly adhered to the support member 54, the sensors and cables can be manufactured over the tubular member 404 on a mandrel. The tubular member 404 with sensors and cables thereon can then be shipped as a separate component instead of being built directly on the looped support member 54. The tubular member material can include a polymer such as polyamide, polyether ether ketone (PEEK), polyimide, or material with similar properties. The tubular member 404 can be adhered to the support member 54 at certain locations (e.g. ends) so that the tubular member 404 has some ability to slide against the support member 54 in non-affixed locations. Additionally, or alternatively, the tubular member 404 can be configured to skew or flex so that a surface of the tubular member 404 adjacent the support member 54 is capable of shifting in relation to an opposite surface to which the sensors and cables are affixed. Further, portions of the cables 409A, 409B, 409C need not be adhered to the tubular member 404 so that those portions are capable of sliding to some degree in relation to the tubular member 404, thereby providing further strain relief.

FIG. 3 illustrates the distal sensor 401A in greater detail. The distal sensor 401A includes an inductive coil 403A including a wire that is wound repeatedly around a predetermined length of the tubular member 404 which surrounds the support member 54. A distal lead 406A to the inductive coil 403A, that is a section of the wire which forms the inductive coil 403A, extends proximally under the coil 403A as illustrated. Alternatively, the distal lead 406A can extend over the coil 403A. The distal lead 406A and a proximal lead 407A of the wire both extend proximally from the coil 403A and are each joined, e.g., by wrapping and/or soldering, to a respective exposed distal end of a respective individual cable 408A of a side-by-side dual cable 409A at a joint region 410A located just proximal of the coil 403A. Alternatively, the distal lead 406A can be joined to an individual cable of the dual cable 408A distal from the coil 403A and the individual cable can cross the coil 403A. The tubular member 404 provides strain relief for the joint region 410A, coil 403A, and dual cable 409A. Optionally, the junction region 410 can include additional strain relief features, such as described in U.S. Pat. Nos. 8,792,962, 10,405,774, and U.S. Patent Publication No. 2020/0015703. (See FIGS. 31-33 of the aforementioned references in particular.) In some examples, the tubular member 404 can provide sufficient strain relief at the joint region 410A so that optional additional strain relief features can be simplified and/or eliminated.

The dual cable 409A can be wound generally transverse, for example, at least two consecutive 720° turns 421A, around the tubular member 404 to anchor the joint region 410A between the coil leads 406A, 407A and the individual cables 408A, 408B, thereby providing additional strain relief to the joint region 410A. Alternatively, these generally traverse dual cable turns 421A can be omitted in examples where the tubular member 404 provides sufficient strain relief.

A protective tube 416, for example, of polyimide, heat shrink, and/or similar material, of sufficient length can be placed over the inductive coil 403A and joint region 410A. Epoxy, UV glue and/or similar material filler 417A can be injected into the tube 416A to fill the space between the tube 416A and the components of the sensor 401A, with excess filler 417A extending distally and proximally of the tube 416A to form end caps 419A on either side of the tube 416A. The proximal end cap 419A can cover at least a portion of the strain relief 720° windings 421A of the dual cable 409A. The filler 417A can further provide support to the distal sensor 401A by potting and fixing the coil 403A and joint region 410A onto the tubing 404 and in the tube 416A. The filler 417A can provide an added degree of rigidity to the distal sensor 401A as further protection against breakage and detachment of wire of the coil 403A and the dual cable 409A.

The dual cable 409A can be wrapped with looser (e.g. diagonal) windings 422A as the dual cable 409A extends proximally from the distal sensor 401A along the tubular member 404. Optionally, additional 720° turns 420A of the dual cable 409A can be positioned in the proximal direction from the proximal end cap 419A to provide additional strain relief. These additional turns 420A are not necessary when the tubular member 404 provides sufficient strain relief.

FIGS. 4 and 5 illustrate the intermediate sensor 401B and the distal sensor 401C respectively, which are formed in a similar manner as the proximal sensor 401A illustrated in FIG. 3. The intermediate sensor 401B and the distal sensor 401C respectively include an inductive coil 403B, 403C having leads 406B, 407B, 406C, 407C connected at a joint region 410B, 410C to individual cables 408B, 408C of a dual cable 409B, 409C covered by a tube 416B, 416C injected with epoxy or other material filler 417B, 417C. Dual wire cables 409A, 409B from the more distal single axis sensors 401A, 401B extend under the inductive coil 403B, 403C of the more proximal single axis sensors 401B, 401C as illustrated. Additionally, or alternatively, the dual wire cables 409A, 409B can extend over the inductive coil 403B, 403C. The portions of dual wire cable 409A, 409B which cross the inductive coils 403B, 403C are electrically insulated from the inductive coils 403B, 403C by insulation of the respective dual cable 409A, 409B. Similarly, each distal lead 406A, 406B, 406C is electrically insulated from its respective inductive coil 403A, 403B, 403C by insulation around the respective distal lead 406A, 406B, 406C. Electrical insulation can be achieved by several means as understood by a person skilled in the pertinent art, and each sensor 401A, 401B 401C can be modified to include alternative electrical insulation.

Referring to FIG. 4, the dual cable 409A from the distal sensor 401A can include one or more traverse turns 421A positioned near the inductive coil 403B of the intermediate sensor 401B distal and/or proximal of the intermediate inductive coil 403B to provide strain relief to this dual cable 409A. The dual cable 409B from the intermediate sensor 401B can include one or more traverse turns 421B near the inductive coil 403B and proximal of the intermediate coil 403B. The traverse turns 421A, 421B near the intermediate coil 403B can be covered by filler 417B similar to as described in relation to FIG. 3. In the proximal direction from the intermediate coil 403B, the dual cable 409A from the distal sensor 401A and the dual cable 409B from the intermediate sensor 401B can be wrapped adjacent to each other. The dual cables 409A, 409B can optionally include additional traverse turns 420A, 420B in the distal and/or proximal direction from the cover of the filler 417B. The dual cables 409A, 409B can include diagonal turns 422A, 422B to travel in the proximal direction along the tubular member 404.

FIG. 5 illustrates the dual cables 409A, 409B, 409C including traverse windings 420A, 420B, 420C, 421A, 421B, 421C and diagonal windings 422A, 422B, 422C following a similar pattern as illustrated in, and described in relation to FIGS. 3 and 4. The dual cables 409A, 409B, 409C can be jointly wound transversely and diagonally as desired proximally toward the elbow 37 (FIG. 2).

Extending over all three single axis sensors between a location immediately distal of the distal sensor 401A and proximal of the elbow 37 but distal of the proximal end of the support member 54 is an outer nonconductive heat shrink tubular member 430.

In manufacturing the nonlinear SAS assembly 400, the distal sensor 401A can be formed over the tubular member 404, followed by the intermediate sensor 401B, and then the proximal sensor 401C. The tubular member 404 can then be slid onto the support member 54. The outer heat shrink tubular member 430 can be affixed over the sensors 401A, 401B, 401C after the sensors are formed over the tubular member 404 and before or after the tubular member 404 is slid over the support member 54. The SAS assembly 400 and support member 54 can be sufficiently flexible to allow movement from a linear delivery shape to a nonlinear deployed shape such as the circular region 39 illustrated in FIG. 1.

FIG. 6 is a top plan view illustration an example catheter 10. The catheter 10 includes the distal end section 15 which is further constructed to include a mapping assembly 27 over the SAS assembly 400, an intermediate deflectable section 14 extending proximally from the distal end section 15, a catheter body 12 extending proximally from the intermediate deflectable section 14, and a control handle 16 at a proximal end of the catheter body 12 which can be used to manipulate the intermediate section 14 and/or distal end section 15 via a deflection arm 75 and/or tension adjustment dial 101. The control handle 16 can be used to manipulate the catheter 10 similar to as described in U.S. Pat. Nos. 8,792,962, 10,405,774, and U.S. Patent Publication No. 2020/0015703 incorporated herein or other such control handle as known to a person skilled in the pertinent art.

Figure 7:
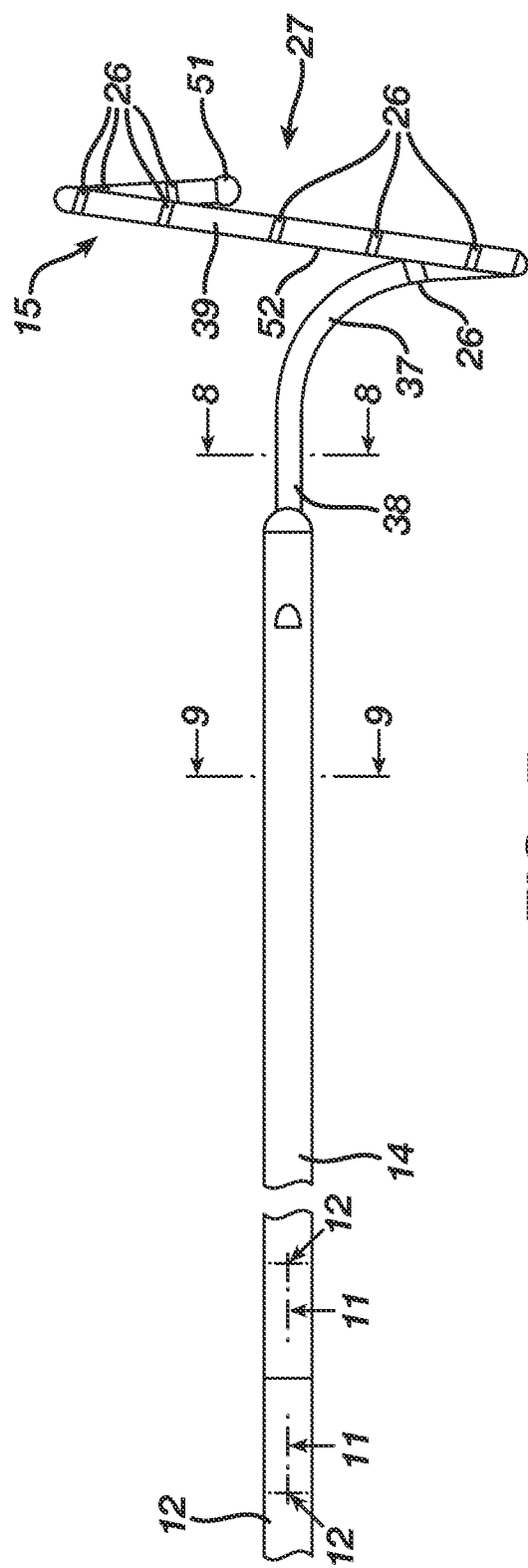
FIG. 7 is a side view illustration of a distal portion of the catheter of FIG. 6, including an intermediate section and a mapping assembly.

FIG. 7 is a side view illustration of the distal end section 15 including the mapping assembly 27 and intermediate section 14. The mapping assembly 27 includes electrodes 26 configured to apply and/or receive electrical signals from tissue at a treatment site. The ring electrodes 26 can be made of any suitable solid conductive material, such as platinum or gold, or a combination of platinum and iridium, and mounted onto a non-conductive cover 52 with glue or the like. Alternatively, the ring electrodes 26 can be formed by coating the non-conductive cover 52 with an electrically conducting material, like platinum, gold and/or iridium. The coating can be applied using sputtering, ion beam deposition or an equivalent technique. A suitable mapping assembly is described in U.S. Pat. No. 7,274,957 incorporated herein by reference and attached in the Appendix of U.S. Provisional Patent Application No. 63/181,641 to which the present application claims priority. If desired, additional electrodes (not shown) can be mounted along the intermediate section 14 and/or a generally straight region 38 of the distal end section 15.

The straight region 38 is mounted on the intermediate section 14 so that it is generally a linear extension of the intermediate section 14. The straight region 38 can have an exposed length, e.g., not contained within the intermediate section 14, ranging from about 3 mm to about 12 mm, more preferably about 3 mm to about 8 mm, still more preferably about 5 mm, but can vary as desired. The elbow 37 is formed between the straight region 38 and the generally circular main region 39 to accommodate the angular transition therebetween.

The generally circular main region 39 is generally traverse, if not also perpendicular, to the catheter body 12. The generally circular main region 39 can form a flat circle or can be helical. The circular main region 39 can have an outer diameter ranging from about 10 mm to about 25 mm, more preferably about 12 mm to about 20 mm, and more preferably about 16 mm. The circular main region 39 can have a circumference ranging from about 30 mm to about 80 mm, more preferably about 38 mm to about 63 mm, and more preferably about 50 mm. The generally circular main region 39 can curve in a clockwise direction or a counterclockwise direction.

Figure 8:
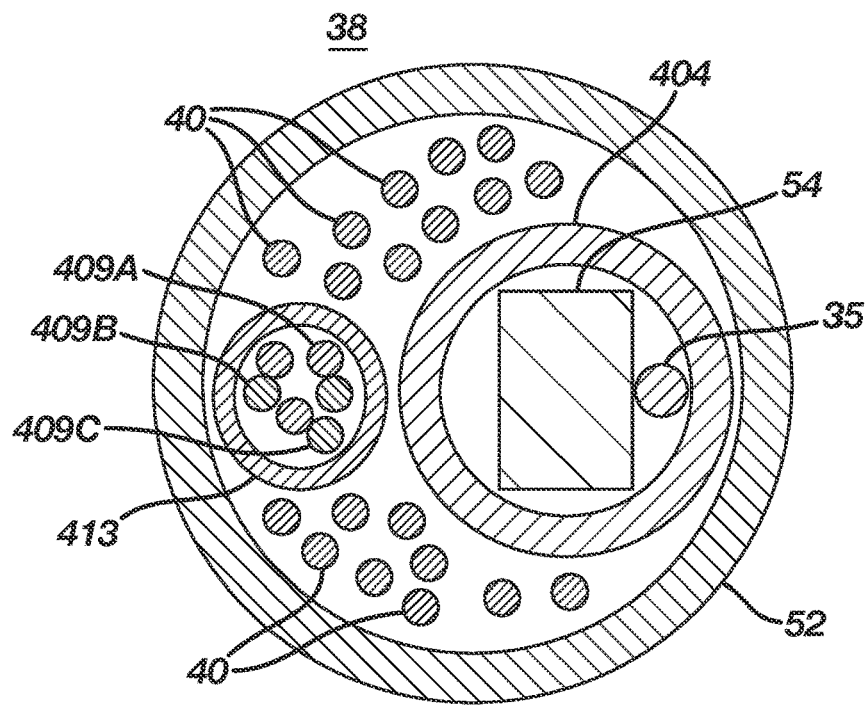
FIG. 8 is a longitudinal cross-sectional view illustration of the mapping assembly of FIG. 7, taken along line 8-8.

FIG. 8 is a cross sectional illustration of the catheter 10 through the straight region 38 of the distal end section 15 as indicated by line 8-8 in FIG. 7. Lead wires 40 to the electrodes 26 of the mapping assembly 27, dual cables 409A, 409B, 409C, the elongated support member 54, and a contraction wire 35 can extend through the non-conductive outer tubing 52. The contraction wire 35 can be manipulated by the handle 16 to resize the circular region 39. The tubular member 404 of the SAS assembly 400 can also extend into the outer tubing 52. The elongated support member 54 and the contraction wire 35 can be positioned within the tubular member 404. The dual cables 409A, 409B, 409C of the SAS assembly 400 can be contained within a protective, non-conductive tube 413.

The outer tubing 52 can have any suitable cross-sectional shape as desired. The outer tubing 52 can be made of any suitable material and is preferably made of a biocompatible plastic such as polyurethane or PEBAX. The outer tubing 52 can be pre-formed into the desired generally circular shape of the generally circular main region 39. Additionally, or alternatively, the shape of the generally circular main region 39 can be defined by a wire or other component extending through the outer tubing 52 such as the support member 54 of the SAS assembly 400.

Figure 9:
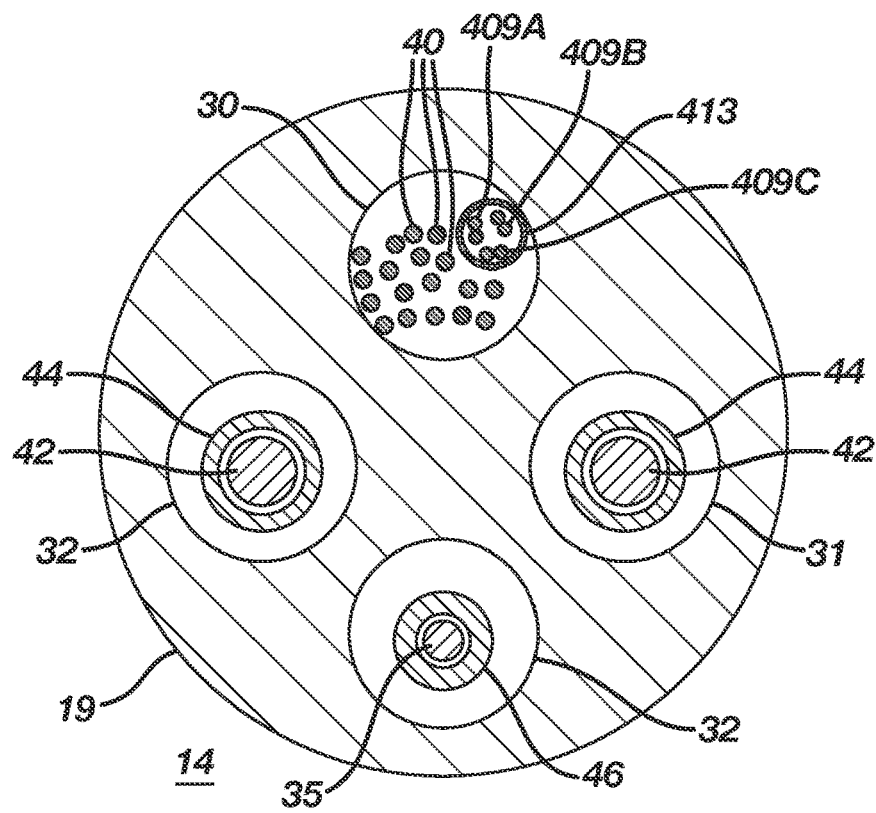
FIG. 9 is a longitudinal cross-sectional view illustration of the intermediate section of FIG. 7, taken along line 9-9.

FIG. 9 is a cross sectional illustration of the catheter 10 through the intermediate section 14 as indicated by line 9-9 in FIG. 7. The intermediate section 14 includes four lumens 30, 31, 32, 33. The intermediate section 14 can be otherwise configured with more or fewer lumens as understood by a person skilled in the pertinent art. The dual cables 409A, 409B, and 409C of the SAS assembly 400 and the lead wires 40 to the electrodes 26 can traverse a first lumen 30 of the four intermediate section lumens. As illustrated, two deflection puller members 42 each respectively extend through opposite lumens 31, 33 of the intermediate section 14 and are each respectively surrounded by a compression coil 44. The deflection puller members 42 can be manipulated by the handle 16 to deflect the intermediate section 14 as illustrated in FIG. 6. A fourth lumen 32 of the intermediate section 14 includes the contraction wire 35 surrounded by another compression coil 46.

Figure 10:
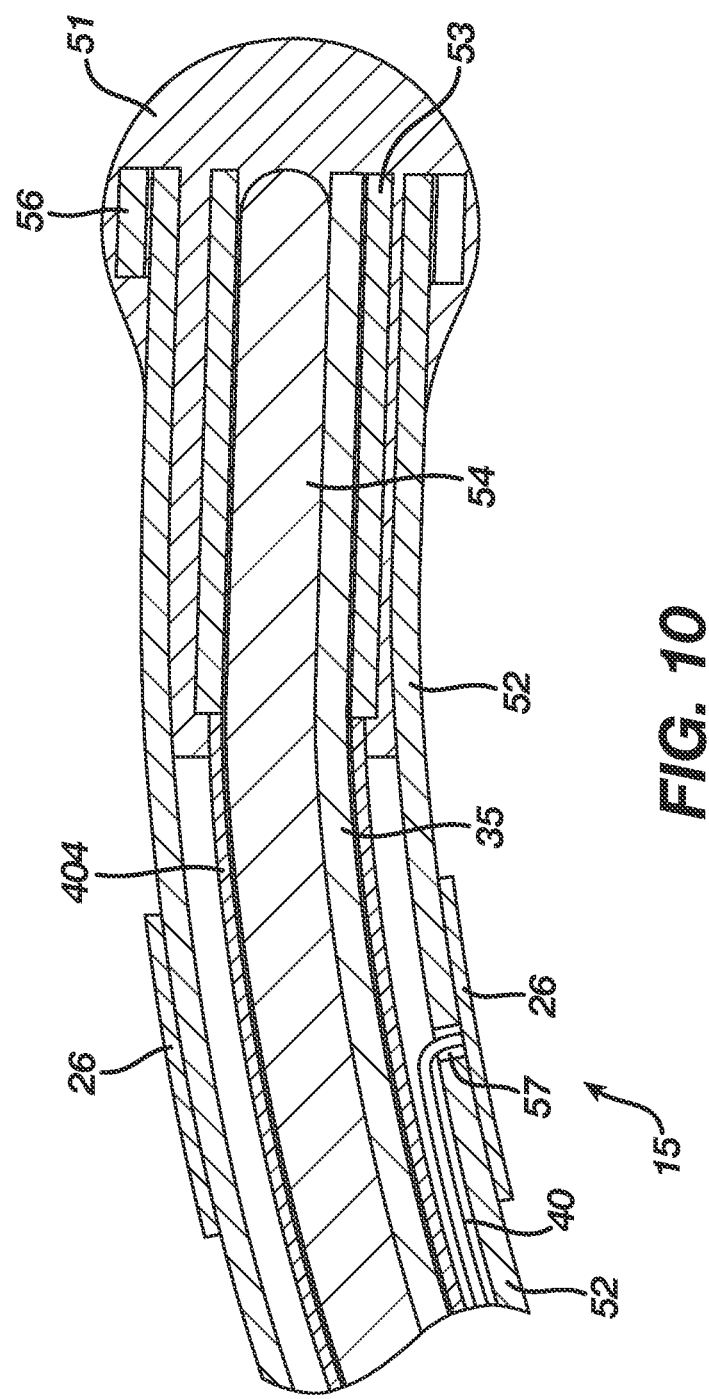
FIG. 10 is a side cross-sectional view illustration of an example distal end of the catheter of FIG. 6.

FIG. 10 is a cross sectional illustration near a distal dome 51 of the distal end section 15. As illustrated, the distal end section 15 is sealed closed with the dome 51. The dome 51 can include polyurethane glue or the like. A short ring 56, made of metal or plastic (e.g., polyamide) is mounted at the distal end of the non-conductive outer tubing 52. The short ring 56 prevents the distal end of the outer tubing 52 from collapsing, thereby maintaining the diameter of the outer tubing 52 at its distal end. Material of the dome can be attached to a length of about 1 mm to about 2 mm of an exterior surface of the outer tubing 52 to anchor the dome 51 to the outer tubing 52.

The support member 54 and the distal end of the contraction wire 35 are soldered or otherwise attached to a small stainless steel tube 53 positioned within the outer tubing 52. With this arrangement, the relative positions of the contraction wire 35 and the support member 54 can be controlled so that the contraction wire can be positioned on the side of the generally circular region 39 closer to the center of the generally circular region 39. The contraction wire 35 on the inside of the curve pulls the support member 54 to the inside of the curve, enhancing contraction of the generally circular region 39. An inner tubing 404 surrounding the support member 54 and contraction wire 35 is preferably the same tubing as the tubular member 404 of the SAS assembly 400, although the inner tubing can be separate from the tubular member 404. The inner tubing 404 can include a braided layer to inhibit the contraction wire 35 from tearing through the inner tubing 404. The outer tubing 52 can include openings 57 through which the lead wires 40 can pass to make electrical contact with the electrodes 26.

Figure 11:
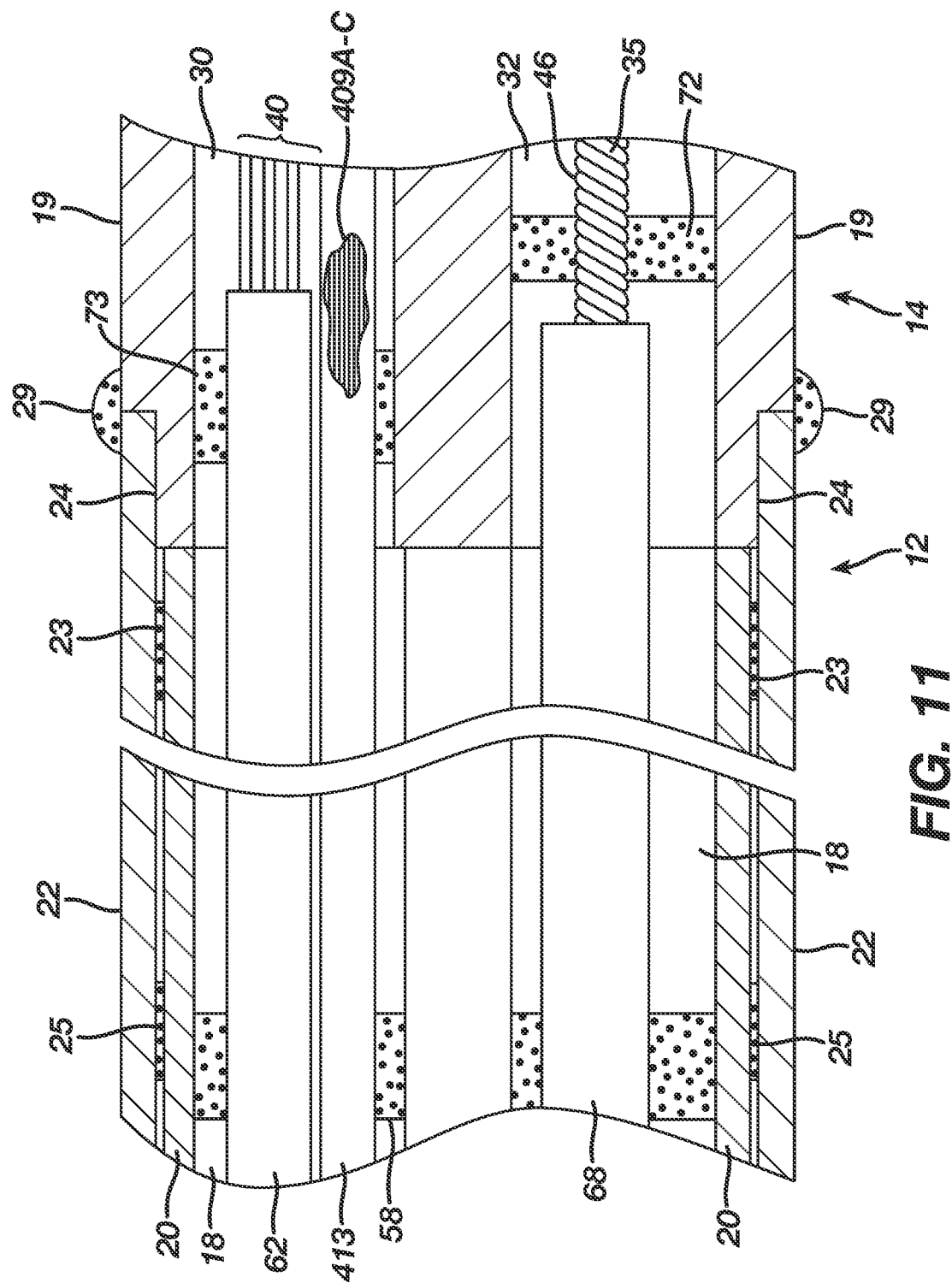
FIG. 11 is a side cross-sectional view illustration of an example junction of a catheter body and an intermediate section, taken along a first diameter.

FIG. 11 is a cross sectional illustration of a junction between the intermediate section 14 and the catheter body 12 as indicated in FIG. 7. The illustrated cross section is taken at a first diameter that is through the first lumen 30 and fourth lumen 32 as oriented vertically in relation to FIG. 9.

Figure 12:
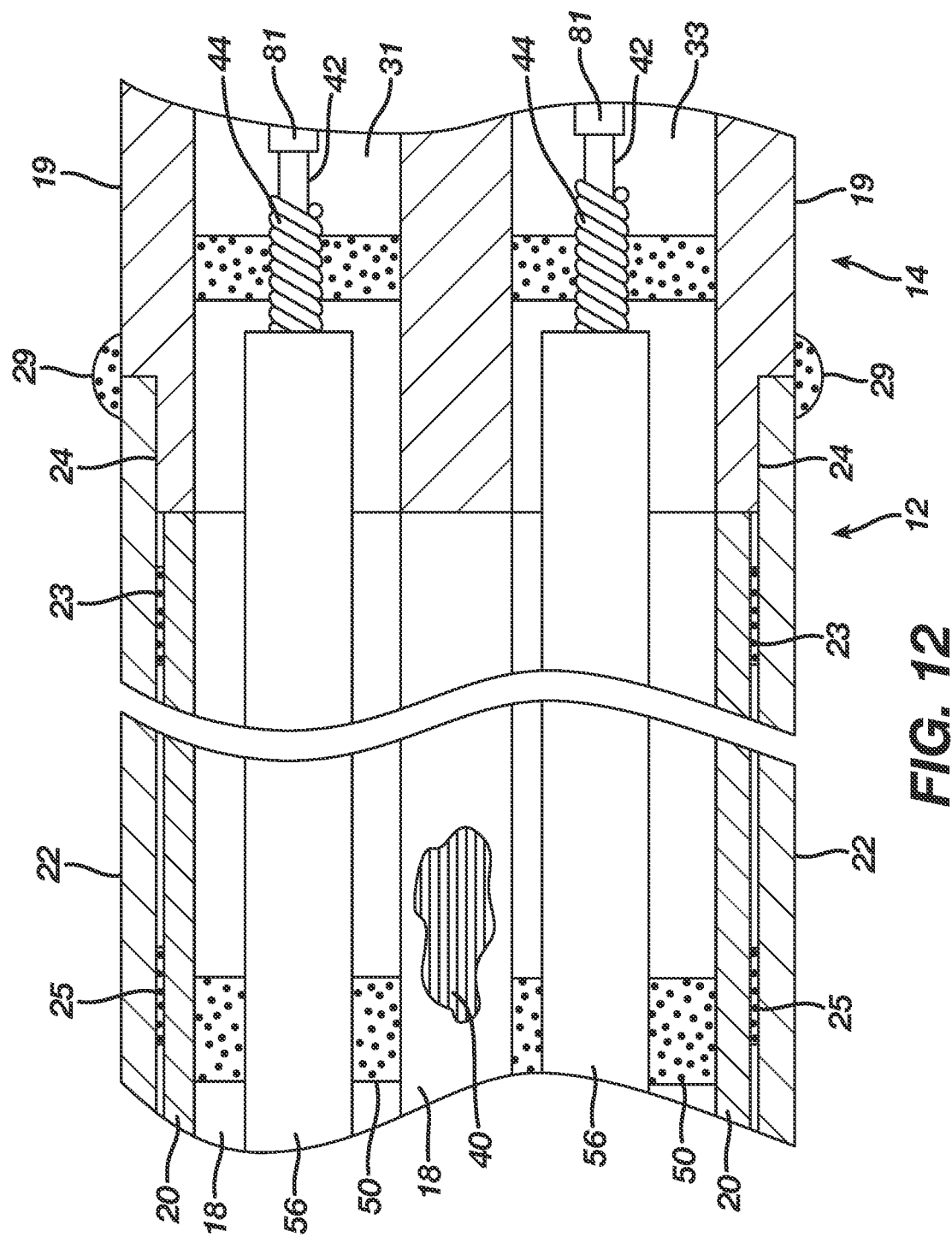
FIG. 12 is a side cross-sectional view illustration of the junction of FIG. 11, taken along a second diameter generally perpendicular to the first diameter.

FIG. 12 is a cross sectional illustration of the junction illustrated in FIG. 11 as indicated in FIG. 7. The illustrated cross section is taken at a second diameter through lumens 31, 33 respectively having a contraction wire 42 extending therethrough, where the second diameter is orthogonal to the first diameter and aligned horizontally in relation to FIG. 9.

Referring collectively to FIGS. 11, and 12, the catheter body 12 can include a single, central or axial lumen 18. The catheter body 12 can be flexible, i.e., bendable, and substantially non-compressible along its length. The catheter body 12 can be of any suitable construction and made of any suitable material. A suitable construction can include an outer wall 22 made of a polyurethane or nylon. The outer wall 22 can include an imbedded braided mesh of stainless steel or the like to increase torsional stiffness of the catheter body 12 so that, when the control handle 16 is rotated, the distal end section 15 of the catheter 10 will rotate in a corresponding manner. A single lumen catheter body 12 may be preferred over a multi-lumen body because the single lumen body can permit better tip control when rotating the catheter 10. The single lumen 18 permits the components passing therethrough to float freely within the catheter body 12. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

The outer diameter of the catheter body 12 is not critical but is preferably no more than about 8 French. Likewise, the thickness of the outer wall 22 is not critical. The inner surface of the outer wall 22 can be lined with a stiffening tube 20, which can be made of any suitable material, e.g., polyimide. The stiffening tube 20 can be held in place relative to the outer wall 22 at the proximal end of the catheter body 12. A first glue joint 23 can be made between the distal ends of the stiffening tube 20 and the outer wall 22 by a fast-drying glue, e.g. Super Glue®. Thereafter a second glue joint 25 can be formed between the proximal ends of the stiffening tube 20 and outer wall 22 using a slower drying but stronger glue, e.g., polyurethane.

The stiffening tube, along with the braided outer wall 22, can provide torsional stability. The outer diameter of the stiffening tube 20 can be about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

The outer wall 22 can have an outer diameter of about 0.092 inch (about 2.3 mm) and an inner diameter of about 0.063 inch (about 1.6 mm) and the polyimide stiffening tube 20 has an outer diameter of about 0.0.029 inch (about 1.56 mm) and an inner diameter of about 0.052 inch (about 1.3 mm).

Referring collectively to FIGS. 9, 11, and 12, the intermediate section 14 can include a shorter section of tubing 19 with multiple off-axis lumens, for example, first, second, third and fourth lumens 30, 31, 32 and 33. The tubing 19 can be made of a suitable non-toxic material which is preferably more flexible than the catheter body 12. A suitable material for the tubing 19 can be braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch, 2.3 mm) and the lumens are generally about the same size, having a diameter of about 0.022 inch (about 0.56 mm), or selected lumens can have a slightly larger diameter of about 0.036 inch (about 0.91 mm).

The proximal end of the intermediate section 14 can include an inner counter bore 24 that receives the outer surface of the polyimide stiffener 20. The intermediate section 14 and catheter body 12 can be attached by glue 29 or the like.

Various components, such as lead wires 40, dual cables 409A, 409B, 409C, and contraction wires 35, 42 can extend through the single lumen 18 of the catheter body 12. Longitudinal movement of the contraction wires 35, 42 to the catheter body 12 enable user control of various parts of the catheter via the control handle 16. Distal ends of the deflection puller members 42 can be anchored to the wall of the tubing 19 near the distal end of the intermediate section 14. In the intermediate section 14, each of the deflection puller members 42 extends through a plastic, e.g., Teflon®, tubular member 81, which prevents the deflection puller members 42 from cutting into the wall of the tubing 19 of the intermediate section 14 when the intermediate section 14 is deflected.

Compression coils 44 can surround the deflection puller members 42 and can extend from the proximal end of the catheter body 12 to the proximal end of the intermediate section 14. The compression coils 44 can be made of any suitable metal, e.g., stainless steel. The compression coils 44 can each be tightly wound on itself to provide flexibility, i.e., bending, but to resist compression. The inner diameter of the compression coils 44 is preferably slightly larger than the diameter of the puller wires 42. For example, when a puller member 42 has a diameter of about 0.007 inches (about 0.18 mm), the corresponding compression coil 44 preferably has an inner diameter of about 0.008 inches (about 0.20 mm). The Teflon® coating on the puller member 42 allows each puller member 42 to slide freely within the corresponding compression coil. The outer surface of the compression coils can be covered by a flexible, non-conductive tubular member to prevent contact between the compression coils and other components, such as lead wires and cables, etc. A non-conductive tubular member can be made of polyimide tubing or other suitable material.

The compression coils 44 can be anchored at their proximal ends to the proximal end of the stiffening tube 20 in the catheter body 12 by a glue joint 50 and at its distal end near the proximal end of the intermediate section 14 in the second lumen 31 and fourth lumen 33 by glue joints 51.

A third compression coil 46 can be situated within the catheter body 12 and intermediate section shaft 14 surrounding the contraction wire 35 (FIG. 8A). The third compression coil 46 extends from the proximal end of the catheter body 12 to near the distal end of the third lumen 32 of the intermediate section 14. The third compression coil 46 can be made of any suitable metal, e.g., stainless steel, and is tightly wound on itself to provide flexibility, i.e., bending, but to resist compression. The inner diameter of the third compression coil 46 is preferably slightly larger than the diameter of the contraction wire 35. The outer surface of the compression coil 46 can be covered by a flexible, non-conductive tubular member 68, e.g., made of polyimide tubing. The third compression coil 46 can be formed of a wire having a square or rectangular cross-sectional area, which makes it less compressible than a compression coil formed from a wire having a circular cross-sectional area. As a result, the third compression coil 46 can be configured to keep the catheter body 12, and particularly the intermediate section 14, from deflecting when the contraction wire 35 is manipulated to contract the mapping assembly 17 as it absorbs more of the compression.

The third compression coil 46 can be anchored at its proximal end to the outer wall 22 of the catheter body 12 by the proximal glue joint 50 and to the intermediate section 14 by distal glue joint 72.

The lead wires 40 attached to the ring electrodes 26 extend through the first lumen 30 of the intermediate section 14, through the central lumen 18 of the catheter body 12, through the control handle 16, and terminate at their proximal end in a connector (not shown) which is connected to an appropriate monitor or other device for receiving and displaying the information received from the ring electrodes 26. The portion of the lead wires 40 extending through the central lumen 18 of the catheter body 12, control handle 16 and proximal end of the intermediate section 14 is enclosed within a protective tubular member 62, which can be made of any suitable material, such as polyimide. The protective tubular member 62 is anchored at its distal end to the proximal end of the intermediate section 14 by gluing it in the lead wire lumen 30 with polyurethane glue or the like to form glue joint 73.

The lead wires 40 are attached to the ring electrode 26 by any conventional technique. In one embodiment, each ring electrode 26 is mounted by first forming a hole in the non-conductive cover 52. An electrode lead wire 40 is fed through the hole, and the ring electrode 26 is welded in place over the lead wire and non-conductive cover 52.

FIGS. 13A through 13E illustrate steps of constructing a distal end of the example catheter 10. FIG. 13A illustrates the SAS assembly 400 over a mandrel 500. The tubular member 404 is placed over the mandrel 500. The sensors 401A, 401B, 401C and the cables 409A, 409B, 409C can be mounted to the tubular member 404 while the tubular member 404 is over the mandrel 500. FIG. 13A includes a cut-out for the purposes of illustration showing a cable 409A wound over the tubular member 404. The mandrel is illustrated having a substantially linear geometry. Alternatively, the mandrel can have a non-linear geometry to facilitate movement of the SAS assembly 404 from the linear configuration to the nonlinear shape when the distal portion 15 of the catheter 10 is deployed.

FIG. 13B is a cross-sectional view of the mid encapsulated SAS 401B as indicated in FIG. 13A. The sensors 401A, 401B, 401C and the cables 409A, 409B, 409C can be secured to the tubular member 404 by a protective tube 416A, 416B, 416C (for example, of polyimide, heat shrink, and/or similar material) and an adhesive 417A, 417B, 417B (for example epoxy, UV glue and/or similar material). The protective tubes 416A, 416B, 416C can extend only over the coils 403A, 403B, 403C such as illustrated in FIGS. 3 through 5. Optionally, the SAS assembly 400 need not include the protective tubes 416A, 416B, 416C, in which case heat shrink 430 or other tubing extending over the length of the SAS assembly 400 can function to protect the sensors 401A, 401B, 401C.

FIG. 13C illustrates the SAS assembly 400 removed from the mandrel 500. Once the SAS assembly 400 is constructed, it can be shipped as a component that can be assembled with the remainder of the catheter 10.

FIG. 13D illustrates the SAS assembly 400 placed onto a support member 54 in a circular shape.

FIG. 13E is a cross-sectional view of the mid encapsulated SAS 401B as indicated in FIG. 13D.

The distal section 15 of the example catheter 10 illustrated herein can be modified in one or more ways in an effort to reduce breakage of cables 409A, 409B, 409C. In some examples, each dual cable 409A, 409B, 409C can be wound generally transverse for an increased number of consecutive 720° turns 421A, 421B, 421C around the tubular member 404 or around the support member 54. The increased number of traverse turns 421A, 421B, 421C is preferably about 5 to about 9 turns 421A, 421B, 421C and more preferably about 5 to about 7 turns. The number of traverse turns 421A, 421B, 421C can be increased at least on a distal side of each coil 403A, 403B, 403C. The increased number of traverse turns 421A, 421B, 421C can act as reinforcement if epoxy wicks onto the cables 409A, 409B, 409C. The increased number of traverse turns 421A, 421B, 421C can increase thickness of the wire along an axis of high strain. In some examples, a shrink sleeve can be added over the traverse turns 421A, 421B, 421C, and/or the protective tube 416A, 416B, 416C can be extended to completely cover the traverse turns 421A, 421B, 421C. The shrink sleeve and/or extended protective tube 416A, 416B, 416C can mitigate epoxy from wicking onto the cables 409A, 409B, 409C. A transition point 41 (FIG. 16) for wire shield can be positioned on the straight region 38, 738 of the distal end section 15 rather than in the circular region 39 or near the elbow 737, 37 (FIG. 2). By positioning the transition point 41 away from the sharp radii of the elbow 737, 37, cables 409A, 409B, 409C may be less likely to break at the transition point 41. The cables 409A, 409B, 409C are preferably about 50 AWG.

FIG. 14 is a side view of an intermediate sensor 503B of a variation of the example catheter 10. The intermediate sensor 503B is wound about a support member 554. The intermediate sensor 503B and support member 554 can be constructed similar to corresponding components 403B, 54 disclosed elsewhere herein. The illustrated segment includes a first dual cable 508A electrically connected to a distal sensor (not shown, configured similar to distal sensor 403A) positioned in a distal direction (DD) in relation to the intermediate sensor 503B. The first dual cable 508A winds about the support member 554 from the distal sensor in a proximal direction (PD) toward the intermediate sensor 503B. Near a distal side of the intermediate sensor 503B, the first dual cable 508A makes seven (7) consecutive traverse turns 521A of approximately 720° about the support member 554. The increased number of traverse turns 521A can reduce the likelihood of cable breakage at the distal side of the intermediate sensor 503B compared to a construction that is identical but for having a reduced number of traverse turns 521A on the distal side of the intermediate sensor 503B. The support member 554 defines a longitudinal axis L-L of the distal section 15 of the catheter 10 near the intermediate sensor 503B. As the support member 554 moves between a circular configuration and a straight configuration, the increased number of traverse turns 521A on the distal side of the intermediate sensor 503B can provide strain relief for the first dual cable 508A and inhibit range of motion of the support member 554 at the distal side of the intermediate sensor 503B. The increase number of traverse turns can force the wires to align more or less perpendicular to the longitudinal axis L-L of the support member 554. Given that the tensile loads induced by straightening the support member 554 are parallel to the longitudinal axis L-L, having the dual cables perpendicular to this direction can reduce the stress and strain on the cross section of the dual cables.

As illustrated in FIG. 14, the first dual cable 508A can travel over an exterior of the intermediate sensor 503B. Additionally, or alternatively, the first dual cable 508A can travel under the intermediate sensor 503B. A second dual cable 508B can be electrically connected to the intermediate sensor 503B, include one or more traverse turns 531B on the proximal side of the intermediate sensor 503B, and wind in the proximal direction (PD) about the support member 554. Although not shown, the first and/or second dual cable 508A, 508B can include an increased number of traverse turns on the proximal side of the intermediate sensor 503B. The dual cables 508A, 508B can wrap with diagonal windings 522A, 522B between sensors.

The first dual cable 508A and/or second dual cable 508B can similarly be wrapped with an increased number of consecutive traverse turns (compared to FIGS. 1-5) on a distal side of a proximal sensor (not shown, configured similar to proximal sensor 403C) that is in the proximal direction (PD) in relation to the intermediate sensor 503B. The SAS assembly can further include a third dual cable (not shown, configured similar to third dual cable 408C). The first, second, and/or third dual cables can be wrapped with an increased number of consecutive traverse turns on a proximal side of the proximal sensor.

Figure 15:
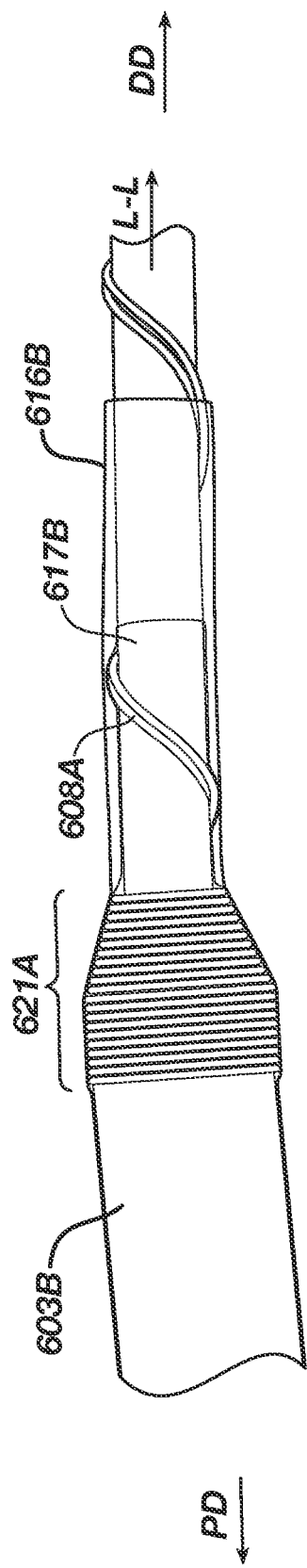
FIG. 15 is a side view illustration of an intermediate sensor of another variation of the example catheter in accordance with the present invention.

FIG. 15 is a side view of an intermediate sensor 603B of another variation of the example catheter 10 showing an increased number of traverse turns 621A (compared to FIG. 14) of a first dual cable 608A positioned on a distal side of the intermediate sensor 603B. The increased number of turns can provide strain relief for the first dual cable 608A and inhibit range of motion of the support member 554 at the distal side of the intermediate sensor 603B. An epoxy, UV glue, and/or similar material filler 617B can be applied over the intermediate sensor 603B and adjacent windings of dual cables (e.g. at least over traverse windings 621A of the first dual cable 608A as illustrated). A protective tube 616B, for example, of polyimide, heat shrink, and/or similar material, of sufficient length can cover the inductive coil 603B adjacent windings, and filler 617B. In some processes, the filler 617B can be injected into the tube 616B similar as described in relation to FIG. 3 with an exception that the filler 617B is completely covered by the protective tube 616B, i.e. the filler 617B does not form end caps 419A on either side of the tube 416A as illustrated in FIG. 3. The filler 617A and protective tube 616B can provide an added degree of rigidity to the intermediate sensor 603B as further protection against breakage of the dual cable 608A. The catheter 10 can be similarly modified at the distal sensor 401A and the proximal sensor 401C. The filler 617B and protective tube 616B can be similarly configured in variations of the catheter 10 having fewer traverse windings such as in FIGS. 3-5 and FIG. 14.

Figure 16:
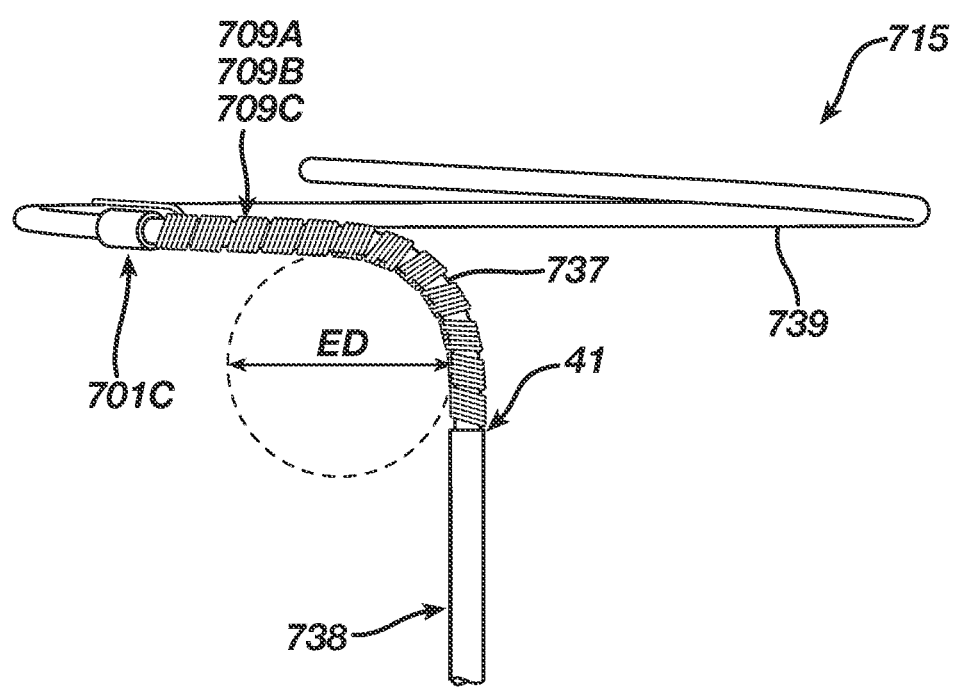
FIG. 16 is a side view illustration of a variation of the example nonlinear single axis sensor assembly shown in FIG. 2 with certain components removed for the sake of illustration in accordance with the present invention.

FIG. 16 is a side view illustration of a variation of the example catheter 10 showing an alternative distal section 715 configuration. Certain components are removed for the sake of illustration. The distal section 715 is constructed similarly to as illustrated in FIG. 2 with an exception that the transition point 41 is positioned on a straight region 738 away from the elbow 37 so that cables 409A, 409B, 409C may be less likely to break at the transition point 41. The distal section 715 includes dual cables 709A, 709B, 709C configured similarly to dual cables disclosed elsewhere herein. The degree of bend of the elbow 737 can be defined by an elbow diameter (ED) as illustrated. The elbow 737 is positioned between a straight region 738 and a circular region 739. According to aspects of the present disclosure, the elbow diameter (ED) can be sized to reduce likelihood of cable break due to flexion of the distal section 715 at the elbow 737. The elbow diameter is preferably greater than 0.18 inches, and more preferably the elbow diameter is about 0.26 to about 0.23 inches in diameter. Strain induced when the distal section 715 moves between a straight configuration and a circular configuration is less for a larger elbow diameter (ED).

The descriptions contained herein are illustrative examples and are not intended in any way to limit the scope of the claimed invention. Examples can be modified, e.g. by utilizing alternative materials and alternative geometries of component parts. Modifications apparent to those skilled in the pertinent art to which this disclosure relates and are intended to be within the scope of the claims which follow.

What is claimed is:

1. A single axis sensor (SAS) assembly comprising:
  a tubular member comprising a lumen therethrough sized to receive an elongated support member suitable for shaping a distal section of a mapping catheter;
  a distal inductive coil affixed to the tubular member and coaxial to the tubular member and comprising leads;
  a first dual cable electrically joined to the leads of the distal inductive coil and wound over the tubular member and an elbow of the distal section of the mapping catheter;
  a proximal inductive coil affixed to the tubular member across the first dual cable, coaxial to the tubular member, and separated from the distal inductive coil such that the distal inductive coil moves in relation to the proximal inductive coil when the tubular member is moved from a linear configuration to a nonlinear configuration; and
  an intermediate inductive coil affixed to the tubular member, coaxial to the tubular member, positioned between the distal inductive coil and the proximal inductive coil when the SAS assembly is in the linear configuration, the first dual cable being wound over a distal end of a first protective tube, the first protective tube covering the intermediate inductive coil.

2. The SAS assembly of claim 1, the nonlinear configuration being approximately circular with a circumference measuring from 24 millimeters 96 millimeters.

3. The SAS assembly of claim 1, the lumen comprising a diameter measuring from 0.08 mm to 0.3 mm.

4. The SAS assembly of claim 1, further comprising:
a second dual cable electrically joined to leads of the intermediate inductive coil and wound over the tubular member to cross the proximal inductive coil.

5. The SAS assembly of claim 1,
the nonlinear configuration being circular, and
the proximal inductive coil, intermediate inductive coil, and distal inductive coil being positioned equidistant around a circumference of the nonlinear configuration.

6. The SAS assembly of claim 1, the first dual cable being wound for 5 to 7 consecutive traverse turns of 720° around the first protective tube covering the intermediate inductive coil and the tubular member adjacent the distal end of the intermediate inductive coil.

7. The SAS assembly of claim 6, further comprising:
a second protective tube positioned to completely cover the traverse turns.

8. The SAS assembly of claim 1, the elbow comprising a diameter of 0.18 inches to 0.26 inches.

9. The SAS assembly of claim 1, further comprising a shrink sleeve extending over the length of the SAS assembly.

10. The SAS assembly of claim 8, further comprising:
a shield wire transition point positioned on a straight region of the elongated support member and away from the elbow, the straight region maintaining a straight configuration when the elongated support member moves to the nonlinear configuration.

11. A mapping catheter comprising:
an elongated support member extending through a distal section of the mapping catheter and comprising a nonlinear predetermined configuration to which the elongated support member moves when the distal section is disposed within a patient; and
a single axis sensor (SAS) assembly comprising:
a tubular member surrounding the elongated support member,
a distal inductive coil affixed to the tubular member and coaxial to the tubular member,
a proximal inductive coil affixed to the tubular member, coaxial to the tubular member, and separated from the distal inductive coil such that the distal inductive coil moves in relation to the proximal inductive coil when the elongated support member moves to the nonlinear predetermined configuration,
a first dual cable electrically joined to leads of the distal inductive coil and wound over the tubular member to cross the proximal inductive coil, the first dual cable further being wound about an elbow of the distal section of the mapping catheter; and
an intermediate inductive coil affixed to the tubular member, coaxial to the tubular member, positioned between the distal inductive coil and the proximal inductive coil when the elongated support member is linearly elongated, the first dual cable being wound over a distal end of a first protective tube, the first protective tube covering the intermediate inductive coil.

12. The mapping catheter of claim 11, the intermediate inductive coil positioned such that the proximal inductive coil, intermediate inductive coil, and distal inductive coil collectively function as a three-axis sensor when the elongated support member moves to the nonlinear predetermined configuration.

13. The mapping catheter of claim 12,
the nonlinear predetermined configuration being circular, and
the proximal inductive coil, intermediate inductive coil, and distal inductive coil being positioned equidistant around a circumference of the nonlinear predetermined configuration.

14. The mapping catheter of claim 13, the nonlinear predetermined configuration comprising a circumference measuring from 10 millimeters to 50 millimeters.

15. The mapping catheter of claim 12, the SAS assembly further comprising:
a second dual cable electrically joined to leads of the intermediate inductive coil and wound over the tubular member to cross the proximal inductive coil.

16. The mapping catheter of claim 12, the first dual cable being wound for 5 to 7 consecutive traverse turns of 720° around the first protective tube covering the intermediate inductive coil and the tubular member adjacent the distal end the tubular member adjacent a side of the respective coil.

17. The mapping catheter of claim 16, the SAS further comprising a second protective tube positioned to completely cover the traverse turns.

18. The mapping catheter of claim 11, the elongated support member comprising a memory shape material heat set to the nonlinear predetermined configuration.

* * * * *